(12) United States Patent
McKenna et al.

(10) Patent No.: US 8,874,180 B2
(45) Date of Patent: Oct. 28, 2014

(54) AMBIENT ELECTROMAGNETIC ENERGY HARVESTING WITH WIRELESS SENSORS

(75) Inventors: Edward M. McKenna, Boulder, CO (US); Daniel Lisogurski, Boulder, CO (US)

(73) Assignee: Covidien LP, Mansfield, MA (US)

( * ) Notice: Subject to any disclaimer, the term of this patent is extended or adjusted under 35 U.S.C. 154(b) by 1248 days.

(21) Appl. No.: 12/714,535

(22) Filed: Feb. 28, 2010

(65) Prior Publication Data

US 2011/0213208 A1    Sep. 1, 2011

(51) Int. Cl.
| | | |
|---|---|---|
| A61B 5/1455 | (2006.01) | |
| A61B 5/00 | (2006.01) | |
| H02J 17/00 | (2006.01) | |
| H01Q 1/24 | (2006.01) | |
| H02J 7/02 | (2006.01) | |

(52) U.S. Cl.
CPC .......... *A61B 5/14552* (2013.01); *A61B 5/681* (2013.01); *A61B 5/6838* (2013.01); *A61B 5/6826* (2013.01); *H02J 7/025* (2013.01); *H02J 17/00* (2013.01); *H01Q 1/248* (2013.01); *A61B 2560/0219* (2013.01); *A61B 2560/0214* (2013.01)
USPC .......................................... 600/323; 600/344

(58) Field of Classification Search
USPC .................. 600/310, 322, 323, 344
See application file for complete search history.

(56) References Cited

U.S. PATENT DOCUMENTS

| | | |
|---|---|---|
| 3,721,813 A | 3/1973 | Condon et al. |
| 4,971,062 A | 11/1990 | Hasebe et al. |
| 4,974,591 A | 12/1990 | Awazu et al. |
| 5,001,685 A | 3/1991 | Hayakawa |
| 5,028,787 A | 7/1991 | Rosenthal et al. |
| 5,035,243 A | 7/1991 | Muz |
| 5,065,749 A | 11/1991 | Hasebe et al. |
| 5,084,327 A | 1/1992 | Stengel |
| 5,094,240 A | 3/1992 | Muz |
| 5,275,159 A | 1/1994 | Griebel |
| 5,348,003 A | 9/1994 | Caro |
| 5,429,129 A | 7/1995 | Lovejoy et al. |

(Continued)

FOREIGN PATENT DOCUMENTS

| | | |
|---|---|---|
| DE | 3516338 | 11/1986 |
| DE | 3703458 | 8/1988 |

(Continued)

OTHER PUBLICATIONS

Crilly, et al.; "An Integrated Pulse Oximeter System for Telemedicine Applications," *IEEE Instrumentation and Measurement Technology Conference*, May 19-21, 1997; pp. 102-104; Ottawa, Canada.

(Continued)

*Primary Examiner* — Eric Winakur
(74) *Attorney, Agent, or Firm* — Fletcher Yoder PC (57) ABSTRACT

A system and method for generating power via harvesting of ambient electromagnetic signals. The system may include one or more sensing components which, acting alone or in combination, are capable of generating data related to one or more physiological parameters. The system may also include wireless communication circuitry capable of wirelessly transmitting the data related to the one or more physiological parameters. Furthermore, at least one of the one or more sensing components or the wireless communication circuitry may be at least partially powered, directly or indirectly, by energy generated via harvested electromagnetic signals.

21 Claims, 6 Drawing Sheets

(56) References Cited

U.S. PATENT DOCUMENTS

| | | | |
|---|---|---|---|
| 5,465,714 A | 11/1995 | Scheuing | |
| 5,474,065 A | 12/1995 | Meathrel et al. | |
| 5,483,646 A | 1/1996 | Uchikoga | |
| 5,511,546 A | 4/1996 | Hon | |
| 5,578,877 A | 11/1996 | Tiemann | |
| 5,619,992 A | 4/1997 | Guthrie et al. | |
| 5,666,952 A | 9/1997 | Fuse et al. | |
| 5,701,894 A * | 12/1997 | Cherry et al. | 600/300 |
| D393,830 S | 4/1998 | Tobler et al. | |
| 5,779,631 A | 7/1998 | Chance | |
| 5,871,442 A | 2/1999 | Madarasz et al. | |
| 6,006,120 A | 12/1999 | Levin | |
| 6,081,742 A | 6/2000 | Amano et al. | |
| 6,144,444 A | 11/2000 | Haworth et al. | |
| 6,261,236 B1 | 7/2001 | Grimblatov | |
| 6,285,895 B1 | 9/2001 | Ristolainen et al. | |
| 6,353,750 B1 | 3/2002 | Kimura et al. | |
| 6,419,671 B1 | 7/2002 | Lemberg | |
| 6,461,305 B1 | 10/2002 | Schnall | |
| 6,512,937 B2 | 1/2003 | Blank et al. | |
| 6,564,088 B1 | 5/2003 | Soller et al. | |
| 6,566,842 B1 * | 5/2003 | Kirkpatrick | 320/101 |
| 6,589,172 B2 | 7/2003 | Williams et al. | |
| 6,591,122 B2 | 7/2003 | Schmitt | |
| 6,791,689 B1 | 9/2004 | Weckström | |
| 6,793,654 B2 | 9/2004 | Lemberg | |
| 6,850,788 B2 * | 2/2005 | Al-Ali | 600/323 |
| 6,916,289 B2 | 7/2005 | Schnall | |
| 6,971,580 B2 | 12/2005 | Zhu et al. | |
| 6,992,751 B2 | 1/2006 | Okita et al. | |
| 7,084,605 B2 * | 8/2006 | Mickle et al. | 320/101 |
| 7,198,778 B2 | 4/2007 | Achilefu et al. | |
| 7,236,811 B2 | 6/2007 | Schmitt | |
| 7,313,427 B2 | 12/2007 | Benni | |
| 7,469,158 B2 | 12/2008 | Cutler et al. | |
| 7,484,129 B1 * | 1/2009 | Varrichio | 714/42 |
| 7,572,229 B2 | 8/2009 | Yeo et al. | |
| 7,574,244 B2 | 8/2009 | Eghbal et al. | |
| 2004/0098009 A1 | 5/2004 | Boecker et al. | |
| 2004/0142733 A1 * | 7/2004 | Parise | 455/572 |
| 2005/0065414 A1 | 3/2005 | Allen et al. | |
| 2005/0075550 A1 | 4/2005 | Lindekugel | |
| 2005/0113656 A1 | 5/2005 | Chance | |
| 2005/0177034 A1 | 8/2005 | Beaumont | |
| 2005/0197548 A1 | 9/2005 | Dietiker | |
| 2005/0228244 A1 * | 10/2005 | Banet | 600/323 |
| 2005/0234317 A1 | 10/2005 | Kiani | |
| 2005/0280531 A1 | 12/2005 | Fadem et al. | |
| 2006/0058594 A1 | 3/2006 | Ishizuka et al. | |
| 2006/0247501 A1 | 11/2006 | Ali | |
| 2006/0282001 A1 | 12/2006 | Noel et al. | |
| 2007/0049842 A1 | 3/2007 | Hill et al. | |
| 2007/0073121 A1 | 3/2007 | Hoarau et al. | |
| 2007/0100218 A1 | 5/2007 | Sweitzer et al. | |
| 2007/0100219 A1 | 5/2007 | Sweitzer et al. | |
| 2007/0106133 A1 | 5/2007 | Satchwell et al. | |
| 2008/0281168 A1 | 11/2008 | Gibson et al. | |

FOREIGN PATENT DOCUMENTS

| | | |
|---|---|---|
| EP | 0127947 | 12/1984 |
| EP | 0531631 | 3/1993 |
| JP | 5049625 | 3/1993 |
| JP | 6014906 | 1/1994 |
| JP | 6269430 | 9/1994 |
| JP | 7236625 | 9/1995 |
| JP | 2000237170 | 9/2000 |
| JP | 2004159810 | 6/2004 |
| JP | 2004329406 | 11/2004 |
| JP | 2004337605 | 12/2004 |
| JP | 2004351107 | 12/2004 |
| WO | WO8909566 | 10/1989 |
| WO | WO9111137 | 8/1991 |
| WO | WO9947039 | 9/1999 |
| WO | WO2005010568 | 2/2005 |
| WO | WO2005114524 | 12/2005 |
| WO | 2006/064399 * | 6/2006 |
| WO | WO2007141121 | 12/2007 |

OTHER PUBLICATIONS

Warren, et al.; "Wearable Sensors and Component-Based Design for Home Health Care," *Proceedings of the Second Joint EMBS/BMES Conference*, Oct. 23-26, 2002; pp. 1871-1872; Houston, Texas.

Lebak, et al.; "Implementation of a Standards-Based Pulse Oximeter on a Wearable, Embedded Platform," *Proceeding of the 25th Annual International Conference of the IEEE EMBS*, Sep. 17-21, 2003; pp. 3196-3198; Cancun, Mexico.

Nagl, et al.; "Wearable Sensor System for Wireless State-of-Health Determination in Cattle," *Proceeding of the 25th Annual International Conference of the IEEE EMBS*, Sep. 17-21, 2003; pp. 3012-3015; Cancun, Mexico.

Pujary, et al.; "Photodetector Size Considerations in the Design of a Noninvasive Reflectance Pulse Oximeter for Telemedicine Applications," *IEEE*, 2003, pp. 148-149.

Wendelken et al.; "The Feasibility of Using a Forehead Reflectance Pulse Oximeter for Automated Remote Triage," *IEEE*, 2004, pp. 180-181.

Hagerty, et al.; "Efficient Broadband RF Energy Harvesting for Wireless Sensors"; *Proc. Govern. Microcircuit Appl. Critical Tech. Conf. (GOMACTech)*, Las Vegas, NV, Apr. 2005, pp. 1-4.

Park; "Overview of Energy Harvesting Systems (for low-power electonics)"; The First Engineering Institute Workshop; Energy Harvesting; Jun. 28, 2005; slides 1-30; Los Alamos National Laboratory.

Mi et al.; "RF Energy Harvesting with Multiple Antennas in the Same Space"; *IEEE Antennas and Propagation Magazine*; Oct. 2005; pp. 100-106; vol. 47, No. 5; IEEE.

Qin et al.; "Microfibre-nonowire hybrid structure for energy scavenging"; Nature; vol. 451; pp. 809-814; Feb. 14, 2008; Nature Publishing Group.

"Prototype Nokia phone recharges without wires"; *The Tech Blog, Yahoo Tech*; Jun. 16, 2009.

* cited by examiner

AMBIENT ELECTROMAGNETIC ENERGY HARVESTING WITH WIRELESS SENSORS

BACKGROUND

The present disclosure relates generally to medical devices and, more particularly, to sensors used for sensing physiological parameters of a patient.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the field of medicine, doctors often desire to monitor certain physiological characteristics of their patients. Accordingly, a wide variety of devices have been developed for monitoring many such physiological characteristics. Such devices provide doctors and other healthcare personnel with the information they need to provide the best possible healthcare for their patients. As a result, such monitoring devices have become an indispensable part of modern medicine.

One technique for monitoring certain physiological characteristics of a patient is commonly referred to as pulse oximetry, and the devices built based upon pulse oximetry techniques are commonly referred to as pulse oximeters. Pulse oximetry may be used to measure various blood flow characteristics, such as the blood-oxygen saturation of hemoglobin in arterial blood, the volume of individual blood pulsations supplying the tissue, and/or the rate of blood pulsations corresponding to each heartbeat of a patient. In fact, the "pulse" in pulse oximetry refers to the time varying amount of arterial blood in the tissue during each cardiac cycle.

Pulse oximeters typically utilize a non-invasive sensor that transmits light through a patient's tissue and that photoelectrically detects the absorption and/or scattering of the transmitted light in such tissue. One or more of the above physiological characteristics may then be calculated based upon the amount of light absorbed or scattered. More specifically, the light passed through the tissue is typically selected to be of one or more wavelengths that may be absorbed or scattered by the blood in an amount correlative to the amount of the blood constituent present in the blood. The amount of light absorbed and/or scattered may then be used to estimate the amount of blood constituent in the tissue using various algorithms.

Wireless sensors have been developed for use in measuring physiological parameters of a patient. Powering of these devices may present a challenge as there are no wires connected to the sensor available to provide power to the sensors. While internal power sources such as batteries may be utilized, problems may exist in which the internal power source is drained. Accordingly, alternate powering methods may be useful.

BRIEF DESCRIPTION OF THE DRAWINGS

Advantages of the disclosed techniques may become apparent upon reading the following detailed description and upon reference to the drawings in which.

DETAILED DESCRIPTION OF SPECIFIC EMBODIMENTS

One or more specific embodiments of the present techniques will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Present embodiments relate to a system and method for harnessing ambient electromagnetic energy into power for powering electronic devices. The system may include one or more electromagnetic sensitive structures that when ambient electromagnetic signals are received at the electromagnetic sensitive structures, harvested electromagnetic charging signals are generated. Ambient electromagnetic signals may include electronic signals generated from, for example, Wi-Fi transmitters, mobile phone antennas, television transmitters, and/or other sources. These ambient electromagnetic signals may be received by the electromagnetic sensitive structures. The received ambient electromagnetic signals may be utilized to generate electromagnetic charging signals therefrom.

The system may utilize the electromagnetic charging signals to charge a power source, such as a rechargeable battery, of a device. Additionally and/or alternatively, the electromagnetic charging signals may be utilized to power the device directly. The device may include, but is not limited to, pulse oximetry sensors, pulse oximetry monitors, portable pulse oximeters, and/or medical implants. That is, the system may include a device with one or more sensing components which, acting alone or in combination, are capable of generating data related to one or more physiological parameters. The system may also include wireless communication circuitry capable of wirelessly transmitting the data related to the one or more physiological parameters. In one embodiment, at least one of the one or more sensing components or the wireless communication circuitry of the device may be at least partially powered, directly or indirectly, by energy harvested through ambient electromagnetic signals received at the electromagnetic sensitive structures.

Figure 1:
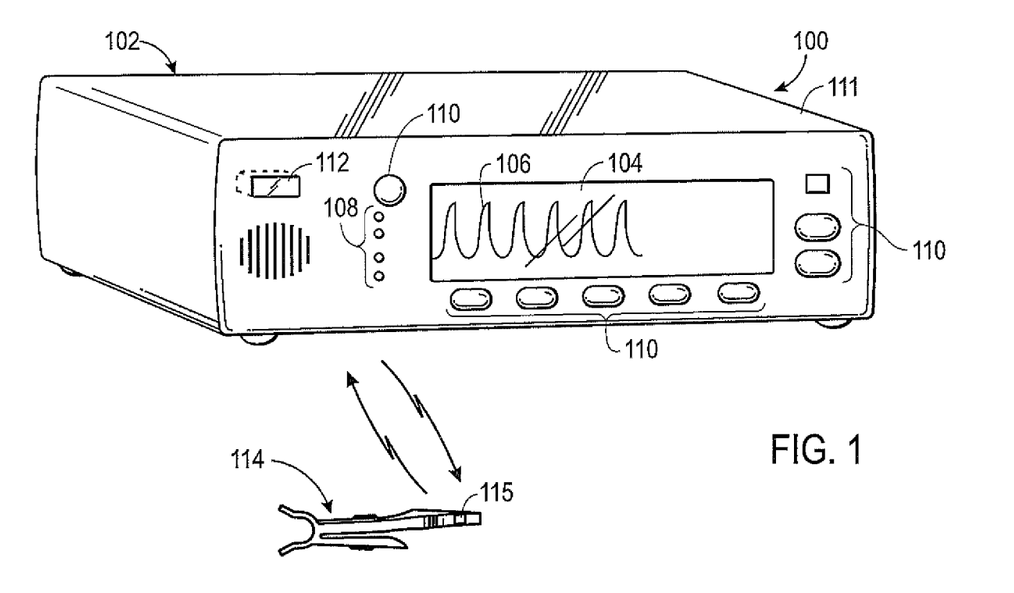
FIG. 1 illustrates a perspective view of a wireless power system including an electronic device, such as a pulse oximeter, in accordance with an embodiment.

Turning to FIG. 1, a perspective view of a medical device is illustrated in accordance with an embodiment. The medical device may be a pulse oximeter 100. The pulse oximeter 100 may include a monitor 102, such as those available from Nelicor Puritan Bennett LLC. The monitor 102 may be configured to display calculated parameters on a display 104. As illustrated in FIG. 1, the display 104 may be integrated into the monitor 102. However, the monitor 102 may be configured to provide data via a port to a display (not shown) that is not integrated with the monitor 102. The display 104 may be configured to display computed physiological data including, for example, an oxygen saturation percentage, a pulse rate, and/or a plethysmographic waveform 106. As is known in the art, the oxygen saturation percentage may be a functional arterial hemoglobin oxygen saturation measurement in units of percentage $SpO_2$, while the pulse rate may indicate a patient's pulse rate in beats per minute. The monitor 102 may also display information related to alarms, monitor settings, and/or signal quality via indicator lights 108.

To facilitate user input, the monitor 102 may include a plurality of control inputs 110. The control inputs 110 may include fixed function keys, programmable function keys, and soft keys. Specifically, the control inputs 110 may correspond to soft key icons in the display 104. Pressing control inputs 110 associated with, or adjacent to, an icon in the display may select a corresponding option. The monitor 102 may also include a casing 111. The casing 111 may aid in the protection of the internal elements of the monitor 102 from damage.

The monitor 102 may further include a transceiver 112. The transceiver 112 may allow for wireless operation signals to be transmitted to and received from an external sensor 114. In this manner, the monitor 102 and the sensor 114 may communicate wirelessly. The sensor 114 may be of a disposable or a non-disposable type. Furthermore, the sensor 114 may obtain readings from a patient that can be used by the monitor 102 to calculate certain physiological characteristics such as the blood-oxygen saturation of hemoglobin in arterial blood, the volume of individual blood pulsations supplying the tissue, and/or the rate of blood pulsations corresponding to each heartbeat of a patient. As will be discussed in greater detail below, the sensor 114 may include a charging device 115, respectively, for harnessing of energy for use by the sensor 114.

Figure 2:
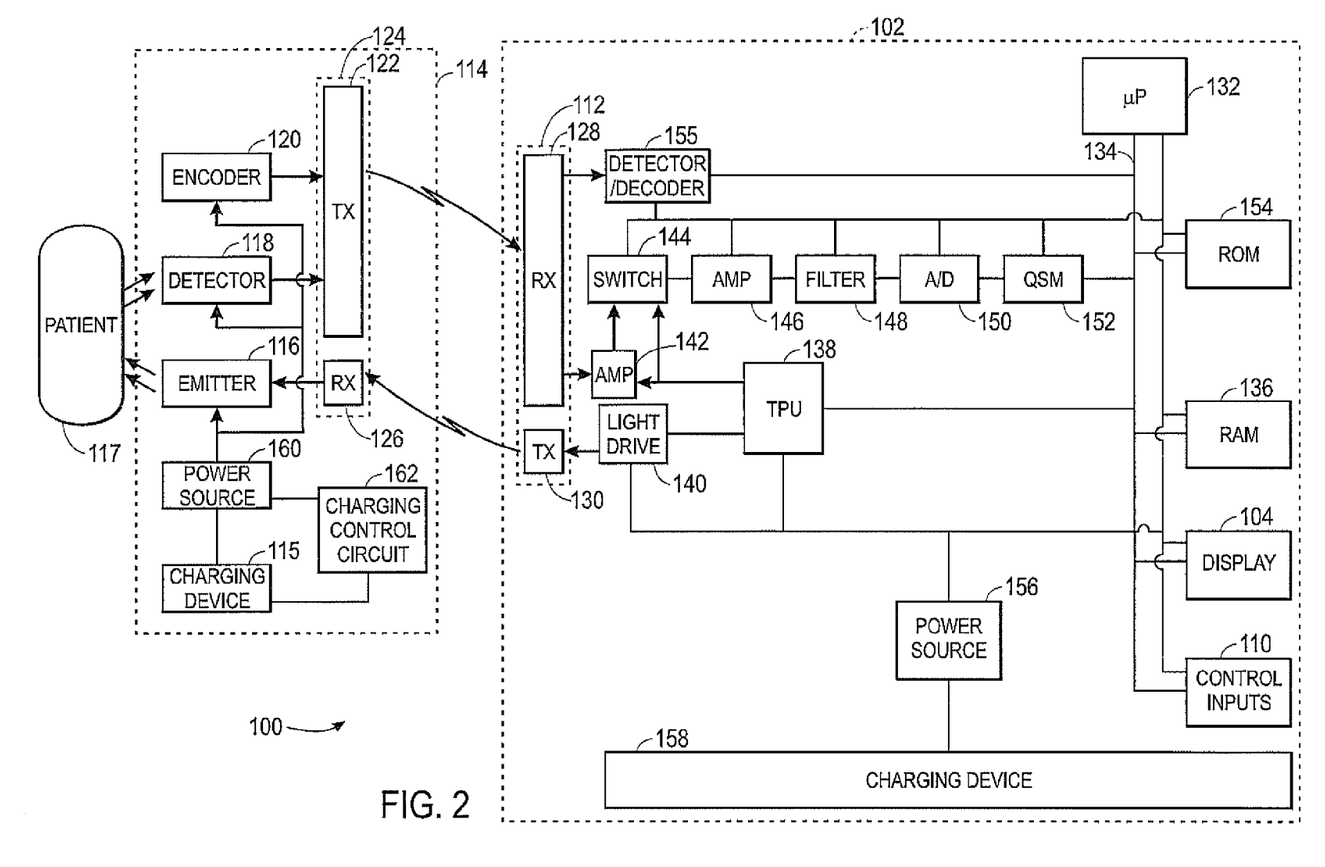
FIG. 2 illustrates a simplified block diagram of the pulse oximeter in FIG. 1, according to an embodiment.

Turning to FIG. 2, a simplified block diagram of the pulse oximeter 100 is illustrated in accordance with an embodiment. Specifically, certain components of the sensor 114 and the monitor 102 are illustrated in FIG. 2. As previously noted, the sensor 114 may include a charging device 115. The sensor 114 may also include an emitter 116, a detector 118, and an encoder 120. It should be noted that the emitter 116 may be capable of emitting at least two wavelengths of light, e.g., RED and infrared (IR) light, into the tissue of a patient 117 to calculate the patient's 117 physiological characteristics, where the RED wavelength may be between about 600 nanometers (nm) and about 700 nm, and the IR wavelength may be between about 800 nm and about 1000 nm. Alternative light sources may be used in other embodiments. For example, a single wide-spectrum light source may be used, and the detector 118 may be capable of detecting certain wavelengths of light. In another example, the detector 118 may detect a wide spectrum of wavelengths of light, and the monitor 102 may process only those wavelengths which are of interest for use in measuring, for example, water fractions, hematocrit, or other physiologic parameters of the patient 117. It should be understood that, as used herein, the term "light" may refer to one or more of ultrasound, radio, microwave, millimeter wave, infrared, visible, ultraviolet, gamma ray or X-ray electromagnetic radiation, and may also include any wavelength within the radio, microwave, infrared, visible, ultraviolet, or X-ray spectra, and that any suitable wavelength of light may be appropriate for use with the present disclosure.

Additionally the sensor 114 may include an encoder 120, which may contain information about the sensor 114, such as what type of sensor it is (e.g., whether the sensor is intended for placement on a forehead or digit) and the wavelengths of light emitted by the emitter 116. This information may allow the monitor 102 to select appropriate algorithms and/or calibration coefficients for calculating the patient's 117 physiological characteristics. Additionally, the encoder 120 may include information relating to the proper charging of the sensor 112. The encoder 120 may, for instance, be a memory on which one or more of the following information may be stored for communication to the monitor 102; the type of the sensor 114; the wavelengths of light emitted by the emitter 116; the proper calibration coefficients and/or algorithms to be used for calculating the patient's 117 physiological characteristics; and/or information regarding a charging device for the sensor 114. The sensor 114 may be any suitable physiological sensor, such as those available from Nellcor Puritan Bennett LLC.

Signals from the detector 118 and the encoder 120 (if utilized) may be transmitted to the monitor 102 via a transmitter 122 that may be located in a transceiver 124. The transceiver 124 may also include a receiver 126 that may be used to receive signals form the monitor 102. As may be seen, the receiver 126 may transmit received signals to the emitter 116 for transmission to a patient 117. The transmitter 122 may receive signals from both the detector 118 and the encoder 120 for transmission to the monitor 102. As previously described, the signals used in conjunction with the emitter 116 and the detector 118 may be utilized for the monitoring of physiologic parameters of the patient 117 while the signals from the encoder may contain information about the sensor 114 to allow the monitor 102 to select appropriate algorithms and/or calibration coefficients for calculating the patient's 117 physiological characteristics.

As previously discussed, the monitor 102 may include a transceiver 112. The transceiver 112 may include a receiver 128 and a transmitter 130. The receiver 128 may receive transmitted signals from the transmitter 122 of the sensor 114 while the transmitter 130 of the monitor 102 may operate to transmit signals to the receiver 126 of the sensor 114. In this manner, the sensor 114 may wirelessly communicate with the monitor 102 (i.e., the sensor 114 may be a wireless sensor 114). The monitor 102 may further include one or more processors 132 coupled to an internal bus 134. Also connected to the bus may be a RAM memory 136 and the display 104. A time processing unit (TPU) 138 may provide timing control signals to light drive circuitry 140, which controls (e.g., via the transmitter 130), when the emitter 116 is activated, and if multiple light sources are used, the multiplexed timing for the different light sources. TPU 138 may also control the gating-in of signals from detector 118 through an amplifier 142 and a switching circuit 134. The amplifier 142 may amplify, for example, the signals from the detector 118 received at the receiver 128. The TPU 138 may control the gating-in of signals from detector 118 through an amplifier 142 to insure that the signals are sampled at the proper time, which may depend at least in part upon which of multiple light sources is activated, if multiple light sources are used. The received signal from the detector 118 may be passed through an (optional) amplifier 146, a low pass filter 148, and an analog-to-digital converter 150 for amplifying, filtering, and digitizing the electrical signals the from the sensor 114. The digital data may then be stored in a queued serial module (QSM) 152, for later downloading to RAM 136 as QSM 152 fills up. In an embodiment, there may be multiple parallel paths of separate amplifier, filter, and AID converters for multiple light wavelengths or spectra received.

In an embodiment, based at least in part upon the received signals corresponding to the light received by detector 118, processor 122 may calculate the oxygen saturation using various algorithms. These algorithms may use coefficients, which may be empirically determined, and may correspond to the wavelengths of light used. The algorithms may be stored in a ROM 154 and accessed and operated according to processor 122 instructions. The monitor 102 may also include a detector/decoder 155 that may receive signals (via the receiver 128) from the encoder 120. The detector/decoder 155 may, for instance, decode the signals from the encoder 120 and may provide the decoded information to the processor 132. The decoded signals may provide information to the processor such as the type of the sensor 114 and the wavelengths of light emitted by the emitter 116 so that proper calibration coefficients and/or algorithms to be used for calculating the patient's 117 physiological characteristics may be selected and utilized by the processor 132.

The monitor 102 may also include a power source 156 that may be used to transmit power to the components located in the monitor 102. In one embodiment, the power source 156 may be one or more batteries, such as a rechargeable battery. The battery may be user-removable or may be secured within the housing of the monitor 102. Use of a battery may, for example, allow the oximeter 100 to be highly portable, thus allowing a user to cany and use the oximeter 100 in a variety of situations and locations. Additionally, the power source 156 may include AC power, such as provided by an electrical outlet, and the power source 156 may be connected to the AC power via a power adapter through a power cord (not shown). This power adapter may also be used to directly recharge one or more batteries of the power source 156 and/or to power the pulse oximeter 100. In this manner, the power adapter may operate as a charging device 158.

The sensor 114 may also include a charging control circuit 162, which may, for example, allow for the adaptive control of wireless energy harvested from the charging device 115 for use in the power source 160 of the sensor 114. In one embodiment, the power source 160 may be one or more batteries, such as a rechargeable battery that may be user-removable or may be secured within the housing of the sensor 114. Alternatively, the power source 160 may be one or more capacitors for storage of charge. The charging control circuit 162 may, for example, include a processing circuit that may determine the current level of charge remaining in the power source 160, as well as the current amount of power being harvested by the charging device. For example, the charging control circuit 162 may determine if the charging device 115 is generating too little power to charge the power source 160. In response to determining that the charging device 115 is generating too little power to charge the power source 160 and that the power source 160 is low on power, the charging control circuit 162 may generate an error signal that may be transmitted to the monitor 102 for generation of a corresponding error message for display on the display 104 of the monitor 102 by, for example, the processor 132. The error message may indicate to a user that the sensor 102 is low on power and may also direct the user to take action, such as changing the power source 160 (i.e., installing new batteries), charging the power source 160 (i.e. by plugging the sensor 102 into a charging unit or into an electrical outlet via a power adapter or, for example, a wired communications port such as a USB port. Alternatively, the error message may indicate to a user that the recharging system of the sensor is potentially malfunctioning, and may direct the user, for example, to use replace the sensor 114. In one embodiment, the error message may be generated when the charging control circuit 162 determines that the power source 160 has reached a certain charge level, for example 20% of the total charge remains in the power source 160. The charging control circuit 162 may also operate to control tuning circuitry of the charging device, as will be described in greater detail below with respect to FIG. 3.

Figure 3:
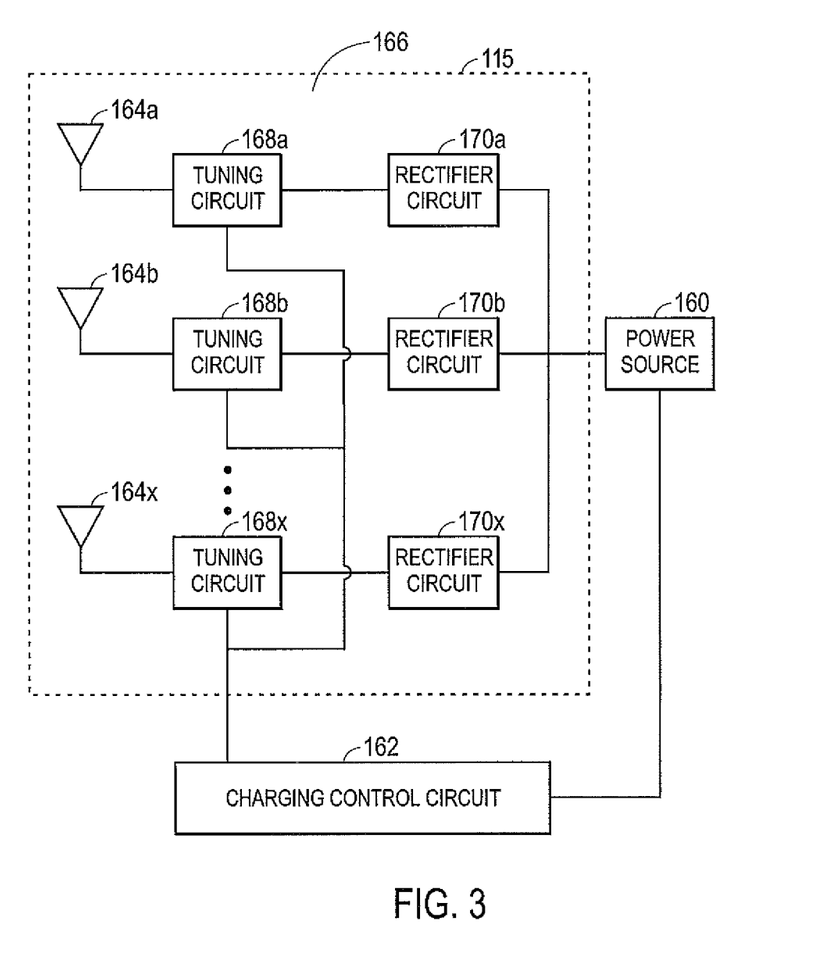
FIG. 3 illustrates a first configuration of the charging device of FIG. 1, in accordance with an embodiment.

FIG. 3 illustrates a first embodiment of the charging device 115. The charging device 115 may include one or more energy harvesting components that utilize, for example, elements for harnessing ambient electromagnetic energy. Through use of these energy harvesting components, power may be harvested, for example, via energy harvesters such as one or more antennas 164a-164x in the charging device 115, and utilized to directly recharge one or more batteries (or capacitors) of the power source 160, and/or to power the sensor 114. The charging device 115 may include, for example, a substrate 166 onto which the one or more antennas 164a-164x may be fabricated. Additionally, one or more tuning circuits 168a-168x, each corresponding to a single one of the antennas 164a-164x, and one or more rectifier circuits 170a-170x may be fabricated on the substrate 166. In one embodiment, the charging device 115, as well as the antennas 164a-164x, tuning circuits 168a-168x, and rectifier circuits 170a-170x, may be, for example, microelectromechanical systems (MEMS) and/or nanoelectromechanical systems (NEMS) made up of components sized between approximately 100 nanometers and 100 micrometers. However, the energy harvester charging device 115, as well as the components that make up the charging device 115 (i.e., antennas 164a-164x, tuning circuits 168a-168x, and rectifier circuits 170a-170x) may also be larger than MEMS and NEMS described above.

The tuning circuits 168a-168x may be, for example, include a tank circuit, that is, an LC circuit including an inductor (L) and a capacitor (C). There may be an inductor and a capacitor connected series with each of the antennas 164a-164x, whereby the inductor and a capacitor are connected in parallel with one another. Upon connection of an antenna, e.g. 164a, to a tuning circuit, e.g. 168a, electric current generated by received ambient electromagnetic signals at the antenna 164a may alternate between the inductor and capacitor at the circuit's resonant frequency (as determined by pre-chosen values for both the inductor and capacitor). In this manner, the given tuning circuit, e.g. 168a, may be able to optimize reception of an ambient electromagnetic signal of a particular frequency for a specific antenna, e.g. 168a. Furthermore, by pre-selecting particular values for each of the tuning circuits 168a-168x to specified values, a plurality of specific ambient electromagnetic signals of particular frequencies may be targeted for reception by the antennas 164a-164x. For example, the antennas 164a-164x and tuning circuits 168a-168x may be tuned to receive various radio frequency (RE) ambient electromagnetic signals. That is, low frequency RF signals from 30-300 kHz, medium frequency RF signals from 300-3000 kHz, high frequency RF signals from HF 3-30 MHz, very high frequency RF signals from 30-300 MHz, ultra high frequency RF signals from 300-3000 MHz, and/or super high frequency RF signals from 3-30 GHz may be targeted for reception by one or more of the antennas 164a-164x. Signals received from any of the bands described above may be received by the antennas 164a-164x, such that the reception results in an electrical current being generated from ambient electromagnetic signals of a particular frequency. The tuning circuits 168a-168x may combine with the antennas 164a-164x to generate an antenna array of tuned antennas 164a-164x each tuned to a different portion of, for example, the RF frequency spectrum for harvesting of energy broadly across that spectrum. For example, the antenna array may be tuned to harvest ambient energy from widely used frequencies such as mobile phone transmissions, wireless communication base station transmissions, Wi-Fi transmissions, television transmissions, and/or radio transmissions.

As noted above, the tuning circuits 168a-168x may be fixed to pre-set levels. However, the tuning circuits 168a-168x may alternatively be variable circuits that may be changed (i.e. tuned) based on current ambient energy reception levels. The charging control circuit 162 may monitor the amount of energy being harvested from each of the antennas 164a-164x and alter the tuning of the respective tuning circuit 168a-168x associated with any of the one or more of the antennas 164a-164x to maximize the energy harvested. For example, antenna 164a may be tuned to receive a low frequency RF signal at, for example, 100 kHz while antenna 164b may be tuned to receive a medium frequency RE signal at, for example, 500 kHz. If the charging control circuit 162 detects that low frequency RE signals are present (indicated by current being generated from antenna 168a) and medium frequency RF signals are not present (indicated by little or no current being generated from antenna 168b), the charging control circuit 162 may operate to adjust the value of the capacitor of tuning circuit 168b to so that reception of a new frequency via antenna 168b may be initiated. This new frequency may be a low frequency RF signal at or near the frequency being received by the antenna 168a. In this manner, as new sources of ambient electromagnetic energy are identified, the charging control circuit may tune respective tuning circuits 168a-168x to optimize reception of the identified ambient electromagnetic frequencies being broadcast.

The electrical current generated via reception of ambient electromagnetic signals described above may correspond to an alternating current (AC) signal. For power storage and utilization, direct current (DC) power may be beneficial. Accordingly, the charging device 115 may also include conversion translation circuitry, such as one or more rectifier circuits 170a-170x, for conversion of alternating current generated via the antennas 164a-164x into direct current. The rectifier circuits 170a-170x may alternatively be located inside of the charging control circuit 162, separate from the antennas 164a-164x and tuning circuits 168a-168x. The rectifier circuits 170a-170x may each, for example, be a full wave rectifier made up of, for example, diodes. The rectification of the electricity by the rectifier circuits 170a-170x may also include smoothing the output of the rectifier circuits 170a-170x. A filter, such as a reservoir capacitor, may be used to smooth the output of the rectifier circuit prior to its transmission to the power storage device 160.

Figure 4A:
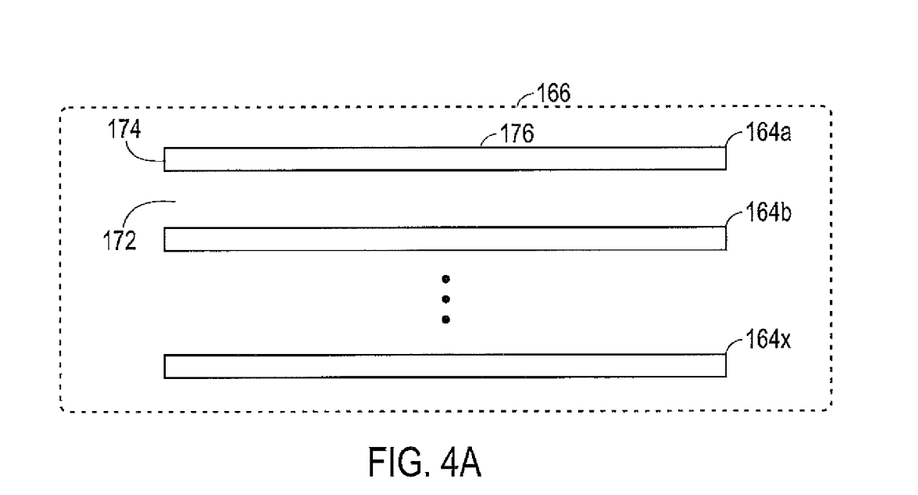
FIG. 4A illustrates a first antenna configuration for use with the first configuration of the charging device of FIG. 1, in accordance with an embodiment.

The antennas 164a-164x themselves may be made of metal such as copper, aluminum, steel, or other conductive composites. Additionally, the alignment and size of the antennas 164a-164x may be modified as required by spatial constraints. FIG. 4A illustrates a first embodiment of the antennas 164a-164x. The antennas 164a-164x may be positioned in a parallel manner with, for example, a gap 172 of approximately 5-20 mm therebetween. Each of the antennas 164a-164x may have a width 174 of approximately 1-10 mm and a length 176 of approximately 10-50 mm. Accordingly, the antennas 164a-164x in FIG. 4A may be of an appropriate size for placement in the sensor 114.

Furthermore, in one embodiment, the width 174 and length 176 of the antennas 164a-164x may be set to predetermined specifications to aid in the tuning of the antennas 164a-164x. However, the parallel configuration of the antennas 164a-164x may exceed available spatial parameters. Accordingly, another configuration of the antennas 164a-164x is illustrated in FIG. 4B.

Figure 4B:
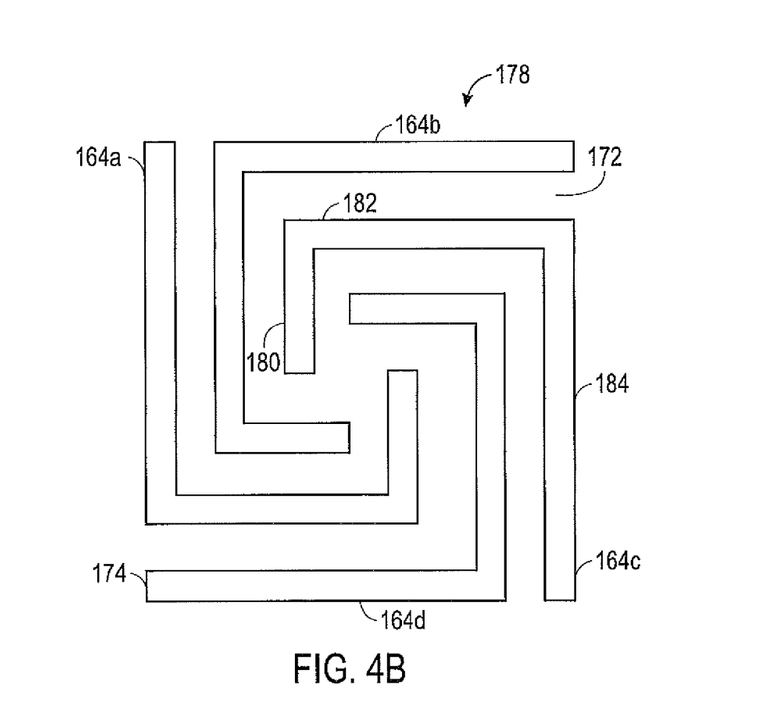
FIG. 4B illustrates a second antenna configuration for use with the first configuration of the charging device of FIG. 1, in accordance with an embodiment.

FIG. 4B illustrates a spiral configuration of four antennas 164a-164d for use as an antenna array 178 in a sensor 114. It should be noted that while four antennas 164a-164d are illustrated, greater than or fewer than four antennas 164a-164x may be utilized in conjunction with the antenna array 178. As illustrated, each of the antennas 164a-164d may be separated by a gap 172 of approximately 5-20 mm therebetween and each of the antennas 164a-164d may have a width 174 of approximately 1-10 mm. Additionally, each of the antennas 164a-164d may have segments constituting the entire length of the antennas 164a-164d. For example, the antennas 164a-164d may each include a first segment 180 with a length of approximately 5-20 mm. The first segment 180 may be electrically coupled to a second segment 182 with a length of approximately 10-30 mm. Additionally, the second segment 182 may be electrically coupled to a third segment 184 with a length of approximately 20-50 mm. By utilizing a spiral pattern for the antenna array 178 multiple antennas, e.g. 164a-164d each with a total length of, for example, 100 mm may be arranged such in such a fashion that no segment includes a length of more than, for example, 50 mm. In this manner, longer antennas capable of receiving more ambient electromagnetic signals may be utilized without extending the overall length of the antenna array 178.

Figure 5:
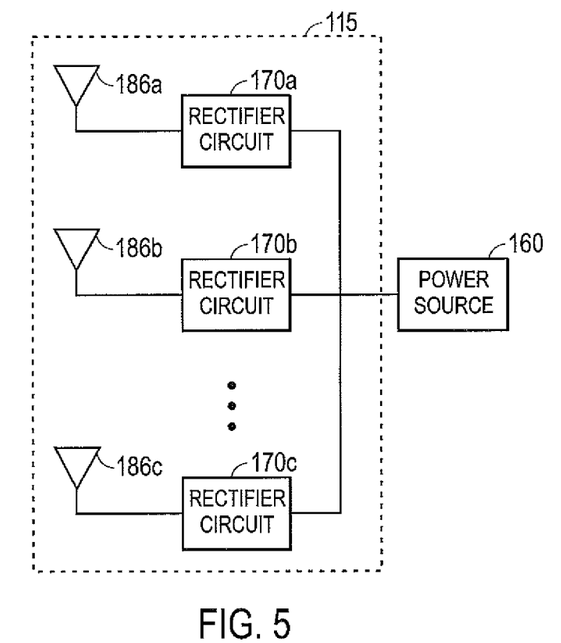
FIG. 5 illustrates a second configuration of the charging device of FIG. 1, in accordance with an embodiment.

FIG. 5 illustrates a second embodiment of the charging device 115 that may operate without tuning circuitry. The charging device 115 may include one or more energy harvesting components that utilize, for example, elements for harnessing ambient electromagnetic energy. Through use of these energy harvesting components, power may be harvested, for example, via energy harvesters such as one or more antennas 186a-186x in the charging device 115, and utilized to directly recharge one or more batteries (or capacitors) of the power source 160 and/or to power the sensor 114. The charging device 115 may include one or more rectifier circuits 170a-170x, similar to those described above with respect to FIG. 3. The antennas 186a-186x may be made of metal such as copper, aluminum, steel, or other conductive composites. Furthermore, the antennas 186a-186x may be fractal antennas of various types and or sizes. For example, antennas 186a-186x may be Sierpinski triangle antennas, Koch curve antennas, and/or fractal tree antennas. Accordingly, antennas 186a-186x may have been shaped in a fractal fashion, that is, split into parts, each of which is approximately a reduced-size copy of the whole.

Moreover, the antennas 186a-186x may constitute broadband antennas; that is, they may be symmetrical about a point, and self-similar (i.e., having the same basic appearance at every scale). At least one advantage of the use of fractal antennas for antennas 186a-186x is that no tuning circuitry is utilized in conjunction with the antennas 186a-186x. This may allow for greater use of the area available, for example, in the sensor 114 to maximize the size and number of antennas 186a-186x utilized while maintaining multiband or broadband performance.

As with antennas 164a-164x, antennas 186a-186x may generate electrical currents via reception of ambient electromagnetic signals. This current may be an alternating current (AC) signal. However, for power storage and utilization, direct current (DC) power may be beneficial. Accordingly, the charging device 115 may also include conversion translation circuitry, such as one or more rectifier circuits 170a-170x, for conversion of alternating current generated via the antennas 186a-186x into direct current. The rectifier circuits 170a-170x may each, for example, be a full wave rectifier made up of, for example, diodes. The rectification of the electricity by the rectifier circuits 170a-170x may also include smoothing the output of the rectifier circuits 170a-170x. A filter, such as a reservoir capacitor, may be used to smooth the output of the rectifier circuit prior to its transmission to the power storage device 160. Furthermore, the rectifier circuits 170a-170x may be located inside of the charging control circuit 162 separate from the antennas 186a-186x.

Figure 6:
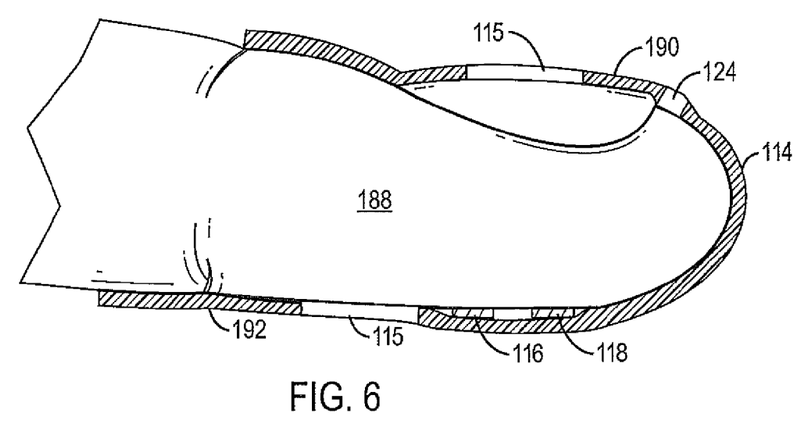
FIG. 6 illustrates a first placement of the charging device and sensor of FIG. 1, in accordance with an embodiment.

The location of the energy harvesters (i.e. antennas 164a-164x and/or antennas 186a-186x) of the charging device 115 may impact the amount of energy harvested from ambient electromagnetic signals. FIG. 6 illustrates various placement locations of one or more charging devices 115 in conjunction with a sensor 114. The sensor 114 may be utilized in conjunction with a finger 188 of a patient 117. As may be seen, the emitter 116 and the detector 118, as well as the transceiver 124 are illustrated as elements of the sensor 114. As depicted, the emitter 116 and detector 118 may be arranged in a reflectance-type configuration in which the emitter 116 and detector 118 are typically placed on the same side of the sensor site. Reflectance type sensors may operate by emitting light into the tissue (e.g., finger 188) and detecting the reflected light that is transmitted and scattered by the tissue. That is, reflectance type sensors detect light photons that are scattered back to the detector 118. The sensor 114 may alternatively be configured as a transmittance type sensor whereby the emitter 116 and detector 118 are typically placed on differing sides of the sensor site. In this manner, the detector 118 may detect light that has passed through one side of a tissue site to an opposite side of the tissue site.

As illustrated in both FIG. 6, the sensor 114 may also include one or more charging stations 115. The charging stations 115 may include antennas 164a-164x and/or antennas 186a-186x, detailed above. In one embodiment, a charging station 115 may be located on a top side 190 of the sensor. Additionally and/or alternatively, a charging station 115 may be located on the bottom side 192 of the sensor 114. Each of these charging stations 115 may be integrated into the sensor 114, or affixed thereto. Furthermore, these charging stations 115 may operate independently, or may be electrically coupled to one another to increase the overall surface area that may be exposed to ambient electromagnetic signals for harvesting for energy. Additionally, one or more charging stations 115 external to the sensor 114 may be utilized.

Figure 7:
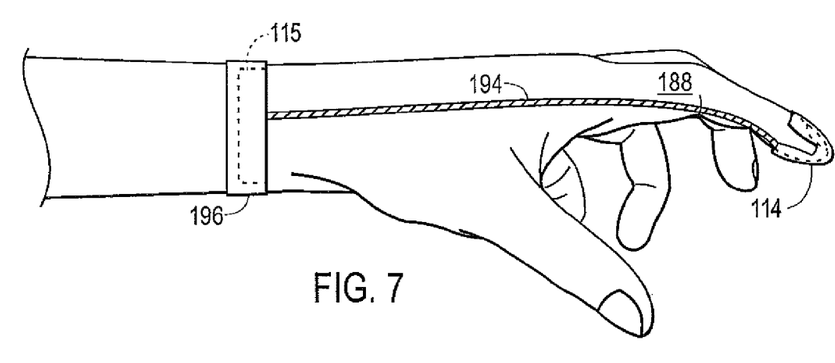
FIG. 7 illustrates a second placement of the charging device and sensor of FIG. 1, in accordance with an embodiment.

FIG. 7 illustrates an embodiment whereby the charging device 115 is located externally from the sensor 114. As illustrated, the charging device 115 may be attached to the sensor 114 via a lead 194. The lead 194 may be an electrical conductor, such as a power cable, that transmits harvested power to the sensor 114. The lead 194 may terminate with the charging device 115 which may be integrated into (or be attached to) a bracelet 196. The bracelet 196 may be, for example, a medical bracelet. Furthermore, the lead 194 may be connected to and separated from the charging device 115. That is, the lead 194 may be separable (i.e., releasable) from the charging device 115, the bracelet 196, and/or the sensor 114. Alternatively, the lead 194 may be permanently affixed to the charging device 115 and/or the bracelet 196. Regardless, by separating the charging device 115 from the sensor 114, more available area in the bracelet 196 may be available for harvesting of energy via ambient electromagnetic signals. That is, with greater area available for the charging device 115, a greater number of antennas 164a-164x and/or antennas 186a-186x may be utilized, thus increasing the overall amount of energy that may be harvested. Additionally, it should be noted that the lead 194 may itself be utilized as an antenna, similar to each of the antennas 164a-164x. Use of the lead 194 as an energy harvester may also aid in increasing the overall area available for harvesting of ambient electromagnetic signals.

Figure 8:
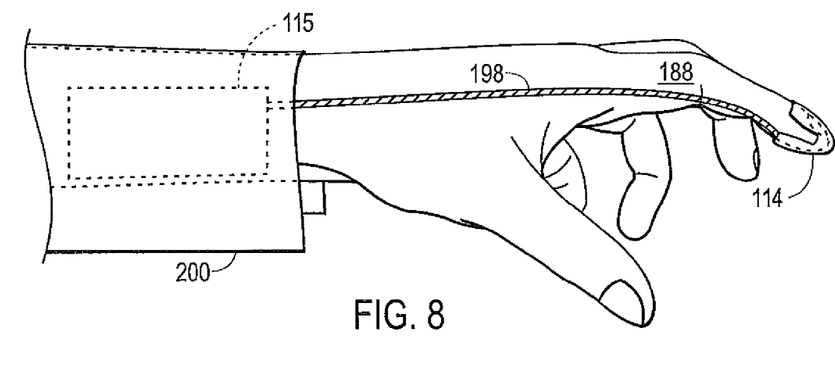
FIG. 8 illustrates a third placement of the charging device and sensor of FIG. 1, in accordance with an embodiment.

Another embodiment of one or more charging stations 115 external to the sensor 114 is illustrated in FIG. 8. As illustrated, the charging device 115 may be attached to the sensor 114 via a lead 198. The lead 198 may be an electrical conductor, such as a power cable, that transmits power to the sensor 114 and may terminate with the charging device 115 which may be integrated into (or be attached to) a garment 200. Again, the lead 198 may be separable (i.e., releasable) from the charging device 115, the garment 200, and/or the sensor 114. Furthermore, the lead may itself be utilized as an antenna, similar to each of the antennas 164a-164x.

The garment 200 may be, for example, a shirt or a sleeve of a shirt. The use of the a garment 200 to house the charging device 115 may allow for the charging device 115 to be expanded in size, or for more than one charging devices 115 to be utilized in conjunction, while still allowing for the garment 200 to be comfortably worn. Thus a greater number of energy harvesting antennas 164a-164x and/or 186a-186x may be utilized, which may increase the overall amount of energy that may be harvested. Additionally, by utilizing a large area, such as the garment 200, a plurality of regions of the patient 117 may be utilized to harvest energy from. That is, the chest, arms, etc. of the patient 117 may be translated into surface area for the placement energy harvesting antennas 164a-164x and/or 186a-186x for use by the sensor 114.

While the disclosure may be susceptible to various modifications and alternative forms, specific embodiments have been shown by way of example in the drawings and have been described in detail herein. However, it should be understood that the embodiments provided herein are not intended to be limited to the particular forms disclosed. Indeed, the disclosed embodiments may not only be applied to measurements of blood oxygen saturation, but these techniques may also be utilized for the measurement and/or analysis of other blood constituents. For example, using the same, different, or additional wavelengths, the present techniques may be utilized for the measurement and/or analysis of carboxyhemoglobin, met-hemoglobin, total hemoglobin, fractional hemoglobin, intravascular dyes, and/or water content. Rather, the various embodiments may cover all modifications, equivalents, and alternatives falling within the spirit and scope of the disclosure as defined by the following appended claims.

What is claimed is:

1. A pulse oximetry sensor, comprising:
a power generating structure configured to generate power to recharge a power source of the pulse oximetry sensor in response to ambient electromagnetic signals, wherein the power generating structure comprises one or more antennas and a charging control circuit, and wherein the charging control circuit is configured to:
determine whether an amount of power generated by each antenna from among the one or more antennas is below a threshold amount of power needed to power the pulse oximetry sensor; and
generate an error signal if the amount of power generated by the power generating structure is below the threshold;

a sensing component configured to generate data related to one or more physiological parameters;

wireless communication circuitry configured to wirelessly transmit the data related to the one or more physiological parameters and configured to wirelessly transmit the error signal, wherein at least one of the sensing component or the wireless communication circuitry are at least partially powered, directly or indirectly, by the power generating structures; and a wired port configured to recharge the power source of the pulse oximetry sensor via an external power source.

2. The pulse oximetry sensor of claim 1, wherein the power source is at least partially charged by the power generating structure, and wherein the sensing component is at least partially powered by the power source.

3. The pulse oximetry sensor of claim 2 wherein the power source comprises a chargeable battery or a capacitor.

4. The pulse oximetry sensor of claim 1, wherein the one or more antennas are fabricated onto a substrate of the power generating structure.

5. The pulse oximetry sensor of claim 1, wherein the power generating structure comprises one or more tuning circuits, and wherein each of the one or more tuning circuit corresponds to each of the one or more antennas.

6. The pulse oximetry sensor of claim 5, wherein each of the one or more tuning circuits is tuned to receive a particular frequency of the ambient electromagnetic signals.

7. A method for powering a wireless pulse oximetry sensor, comprising the acts of:

generating power to recharge a power source of the pulse oximetry sensor using a power generating structure in response to ambient electromagnetic signals, wherein the power generating structure comprises a charging control circuit configured to monitor an amount of power generated by each antenna from among a plurality of antennas;

providing the power to the pulse oximetry sensor;

determining whether the amount of power generated by the power generating structure is below a threshold amount of power needed to power the pulse oximetry sensor; and transmitting an error signal if the amount of power generated by the power generating structure is below the threshold.

8. The method of claim 7, wherein the power is stored in a battery or capacitor prior to being provided to the sensor.

9. The method of claim 7, wherein the power is generated at a location separate from the sensor.

10. The method of claim 9, wherein the location separate from the sensor is at a bracelet or a garment worn by the patient.

11. The method of claim 7, comprising utilizing the power by the sensor to generate data related to one or more physiological parameters of the patient.

12. The method for powering a wireless sensor of claim 7, comprising recharging the power source via an external power source when the amount of power generated by the power generating structure is below the threshold.

13. A monitoring system, comprising:
a pulse oximetry sensor, comprising:
a light generating component;
a light detecting component configured to detect light generated by the light generating component;
a power generating component configured to:
generate power to recharge a power source of the pulse oximetry sensor in response to ambient electromagnetic signals, wherein the generated power is provided to one or more of the light generating component, the light detecting component, or the wireless transmitter;
determine whether an amount of generated power is below a threshold amount of power needed to power the pulse oximetry sensor; and
generate an error signal if the amount of generated power by the power generating structure is below the threshold;
a wireless transmitter configured to wirelessly transmit a signal based on the light detected by the light detecting component and configured to wirelessly transmit the error signal;
a wired port configured to recharge the power source of the pulse oximetry sensor via an external power source; and
a monitor configured to receive the signal and the error signal.

14. The monitoring system of claim 13, wherein the power generating component is incorporated into the wireless sensor.

15. The monitoring system of claim 13, wherein the power generating component is separate from, but in communication with, the wireless sensor.

16. The monitoring system of claim 13, wherein the power source is configured to store the generated power prior to the power being provided to one or more of the light generating component, the light detecting component, or the wireless transmitter.

17. The monitoring system of claim 13, wherein the power generating component comprises a plurality of antennas.

18. The monitoring system of claim 17, wherein the power generating structure comprises one or more tuning circuits, and wherein each of the one or more tuning circuit corresponds to each of the plurality of antennas.

19. The monitoring system of claim 17, wherein the power generating unit comprises a charging control circuit configured to monitor the amount of power generated by the plurality of antennas.

20. The monitoring system of claim 19, wherein the charging control circuit is configured to alter the tuning of each of the one or more tuning circuits based on the amount of power generated.

21. The monitoring system of claim 19, wherein the charging control circuit is configured to transmit the error signal to the monitor if the amount of power generated by the plurality of antennas is below the threshold.

* * * * *